(12) United States Patent
Palo, Jr.

(10) Patent No.: US 9,271,859 B2
(45) Date of Patent: Mar. 1, 2016

(54) BRACE

(76) Inventor: Matti Palo, Jr., Covington, LA (US)

(*) Notice: Subject to any disclaimer, the term of this patent is extended or adjusted under 35 U.S.C. 154(b) by 338 days.

(21) Appl. No.: 13/403,343

(22) Filed: Feb. 23, 2012

(65) Prior Publication Data

US 2013/0226057 A1 Aug. 29, 2013

(51) Int. Cl.
*A61F 5/01* (2006.01)

(52) U.S. Cl.
CPC ..................... *A61F 5/0118* (2013.01)

(58) Field of Classification Search
USPC ........ 602/16, 18, 20–23, 26–27, 64; 128/846; 2/16, 162–163, 170; D24/64, 190; 473/54–55
See application file for complete search history.

(56) References Cited

U.S. PATENT DOCUMENTS

| | | | | |
|---|---|---|---|---|
| 5,004,227 | A * | 4/1991 | Hoffman | 482/105 |
| 5,415,624 | A | 5/1995 | Williams | |
| 5,513,657 | A | 5/1996 | Nelson | |
| 5,538,501 | A * | 7/1996 | Caswell | 602/64 |
| 5,928,172 | A * | 7/1999 | Gaylord | 602/21 |
| 6,013,045 | A | 1/2000 | Gaylord | |
| 6,024,715 | A | 2/2000 | Maxwell | |
| 6,029,277 | A * | 2/2000 | Picchione, II | 2/162 |
| 6,142,966 | A | 11/2000 | Hely | |
| 6,279,159 | B1 | 8/2001 | Ahlbaumer et al. | |
| 6,790,192 | B2 * | 9/2004 | Robinson | 602/21 |
| 7,455,650 | B1 * | 11/2008 | Garelick et al. | 602/21 |
| 8,246,560 | B2 * | 8/2012 | Gaylord et al. | 602/21 |
| 2005/0101898 | A1 | 5/2005 | Cohen | |
| 2005/0267391 | A1 | 12/2005 | Garelick et al. | |
| 2011/0077568 | A1 * | 3/2011 | Brown | 602/21 |

OTHER PUBLICATIONS

PCT/US2013/027302 International Search Report and Written Opinion, mailed Jun. 13, 2013.
International Preliminary Report on Patentability & Written Opinion for PCT/US2013/027302, International Bureau of WIPO, Geneva, CH; mailed Sep. 4, 2014.

* cited by examiner

*Primary Examiner* — Ophelia A Hawthorne
(74) *Attorney, Agent, or Firm* — Harness, Dickey & Pierce, P.L.C.

(57) ABSTRACT

A brace may include a body portion and a finger portion. The body portion may include a first flexible sheet configured to receive at least portions of a user's wrist and hand and may restrict movement of the wrist. The finger portion may include a second flexible sheet attached to the first flexible sheet. The finger portion may be configured to receive at least one of the user's fingers and may restrict movement of the at least one finger relative to the wrist and hand.

8 Claims, 4 Drawing Sheets

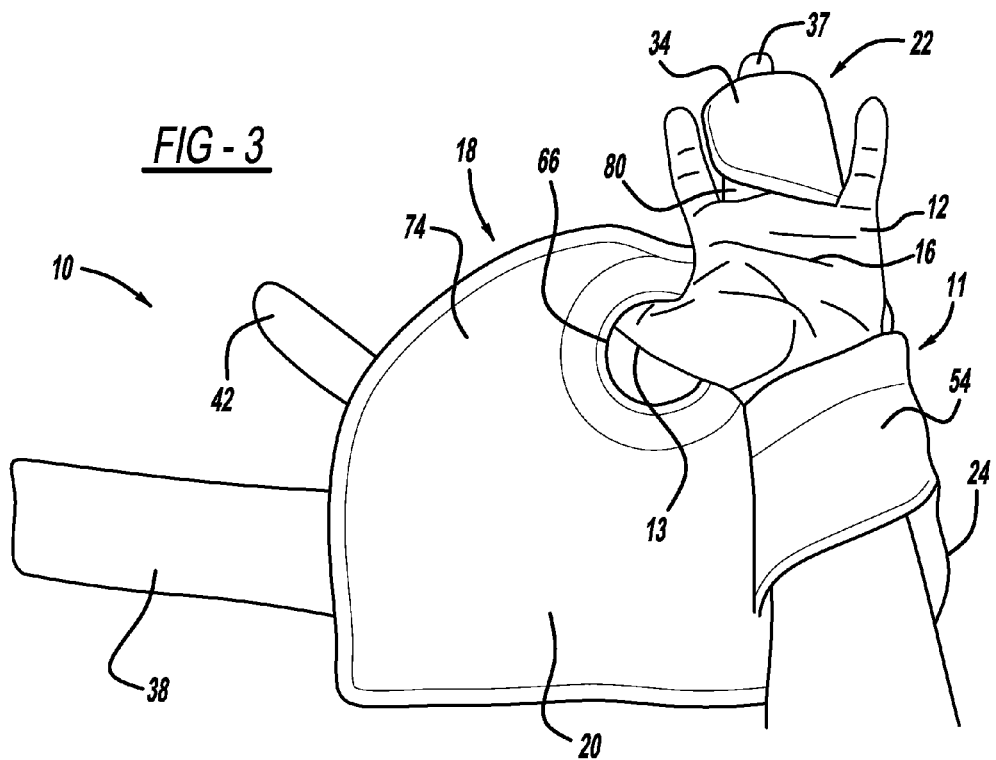
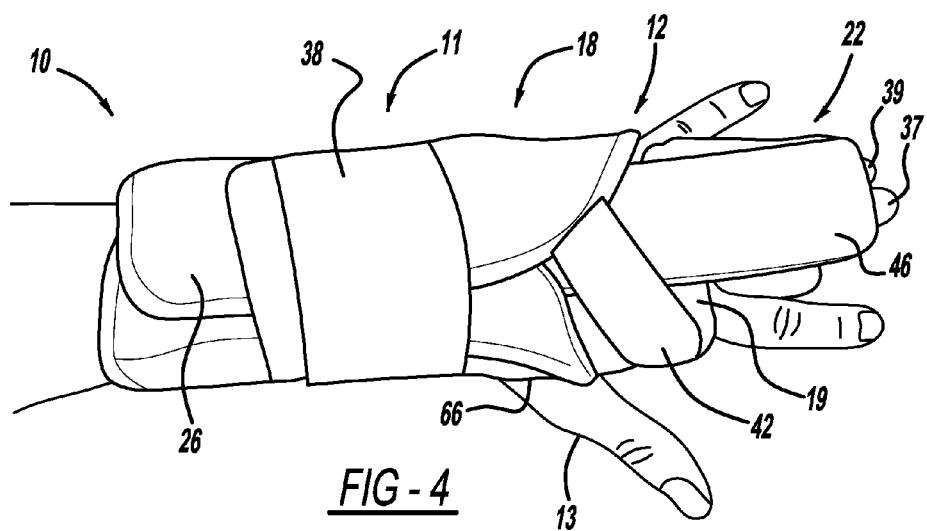

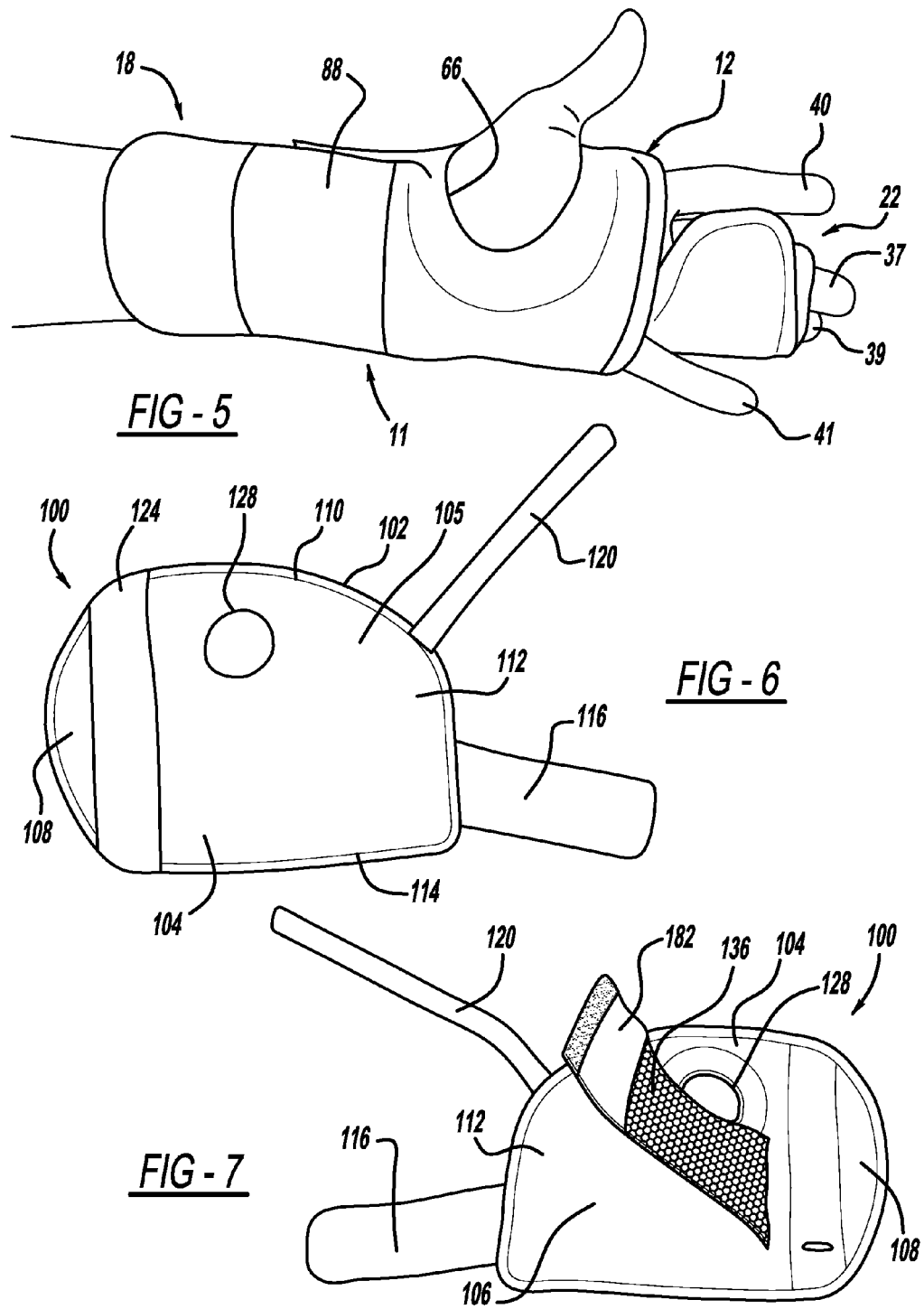

BRACE

FIELD

The present disclosure relates to a therapy brace.

BACKGROUND

This section provides background information related to the present disclosure which is not necessarily prior art.

A human hand may include a median nerve that supplies muscle function and sensation to a thumb, an index finger, and half of a ring finger. Median neuropathy, known as carpal tunnel syndrome, leads to wasting of the thumb musculature (thenar eminence) and resultant weakness that may become permanent if left untreated. Furthermore, median neuropathy can cause numbness in the digits that may be permanent if untreated. A brace can be used to splint or support at least a portion of the hand, fingers and/or wrist as an alternative to or in addition to a surgical procedure to treat median neuropathy and/or other nerve, muscle and/or joint conditions.

SUMMARY

This section provides a general summary of the disclosure, and is not a comprehensive disclosure of its full scope or all of its features.

In one form, the present disclosure provides a brace that may include a body portion and a finger portion. The body portion may include a first flexible sheet configured to receive at least portions of a user's wrist and hand and that restricts movement of the wrist. The finger portion may include a second flexible sheet attached to the first flexible sheet. The finger portion may be configured to receive at least one of the user's fingers and may restrict movement of the at least one finger relative to the wrist and hand.

In another form, the present disclosure provides a brace that may include a flexible sheet having a first side and a second side. The first side may receive at least a portion of a user's wrist and hand. A rigid panel may be attached to the flexible sheet at a location that corresponds to a dorsal side of a user's wrist and hand. The rigid panel may cooperate with the flexible sheet to restrict movement of the wrist.

In another form, the present disclosure provides a brace that may include a flexible sheet having a first side and a second side. The first side may receive at least a portion of a user's wrist and hand. An inner strap may be attached to the first side of the flexible sheet and may be configured to be wrapped at least partially around the user's wrist to secure the flexible sheet thereon. The inner strap may be configured to receive an insert including at least one of a heating element and a cooling element.

In another form, the present disclosure provides a therapy kit that may include a first brace and a second brace. The first brace may include a first body portion configured to be wrapped around a user's wrist and restrict movement of the wrist. The first brace may allow relative movement of the user's fingers relative to the wrist. The second brace may include a second body portion and a finger portion. The second body portion may be configured to be wrapped around the user's wrist and restrict movement of the wrist. The finger portion may be attached to the body portion and may be configured to receive at least one of the user's fingers and may restrict movement of the at least one finger relative to the wrist.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a perspective view of the brace secured to a user's limb in a first condition;

FIG. 4 is a perspective view of the brace secured to the user's limb in a second condition;

FIG. 5 is another perspective view of the brace secured to the user's limb in the second condition;

FIG. 6 is a plan view of a first side of another brace according to the principles of the present disclosure;

FIG. 7 is a plan view of a second side of the brace of FIG. 6;

Corresponding reference numerals indicate corresponding parts throughout the several views of the drawings.

DETAILED DESCRIPTION

Figure 1:
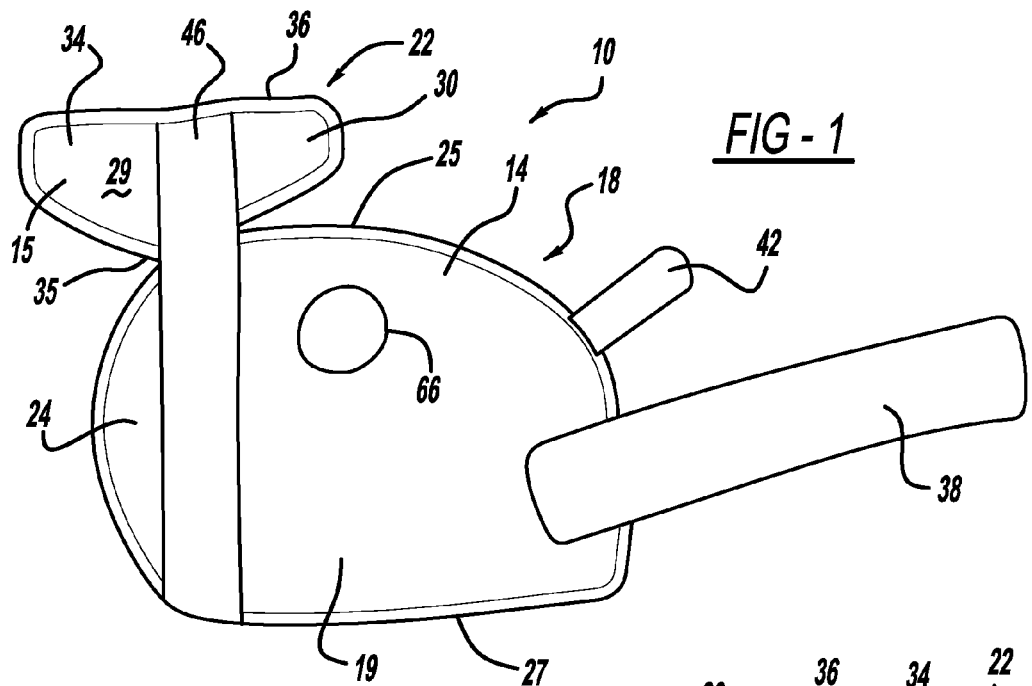
FIG. 1 is a plan view of a first side of a brace according to the principles of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference to FIGS. 1-5, the present disclosure provides a brace 10 configured to be secured to a user's wrist 11 and hand 12. The brace 10 may be used to treat injuries or conditions (for example only, carpel tunnel syndrome). The brace 10 may include a body portion 18, a finger portion 22, and a spar 46. The body portion 18 and the finger portion 22 may be formed from first and second flexible sheets 14, 15, respectively. The first and second flexible sheets 14, 15 may be formed from a fabric material such as a foam material, for example, and may be capable of bi-directional elastic deformation. In some embodiments, the body portion 18 and the finger portion 22 could be formed from a single, unitary flexible sheet.

Figure 2:
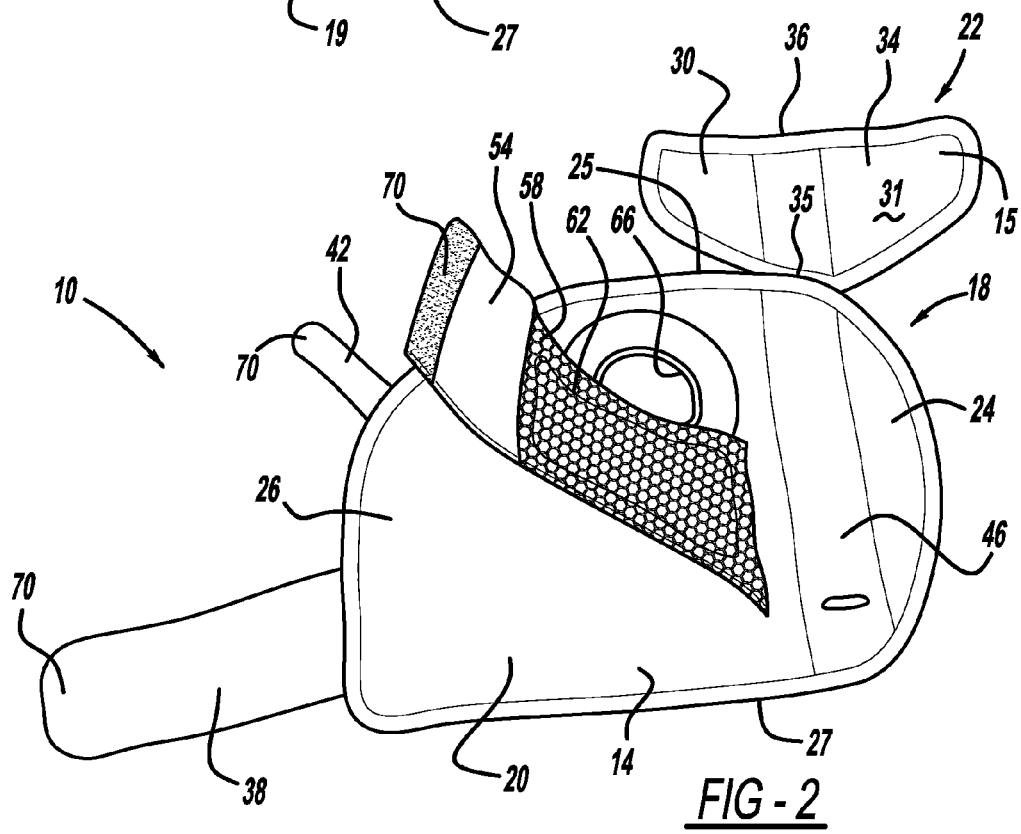
FIG. 2 is a plan view of a second side of the brace of FIG. 1.

The body portion 18 may include a first side 19 (shown in FIG. 1) and a second side 20 (shown in FIG. 2). The first and second sides 19, 20 may cooperate to form a first lateral end 24, a second lateral end 26, a first edge 25, and a second edge 27. An aperture 66 may be formed in the body portion 18 between the first and second lateral ends 24, 26 and may extend through the first and second sides 19, 20. In some embodiments, the aperture 66 may be disposed closer to the first edge 25 than the second edge 27.

The body portion 18 may also include a first outer strap 38, a second outer strap 42, and an inner strap 54. The first and second outer straps 38, 42 can be attached to the body portion 18 at or near the second lateral end 26. The first and second outer straps 38, 42 may be releasably secured to the first side 19 of the body portion 18 via a buckle (not shown) or via hook-and-loop retaining means (e.g., VELCRO®) or any other suitable retaining means to secure the body portion 18 to the user's wrist 11 and hand 12, as shown in FIGS. 4 and 5.

The inner strap 54 may extend from the second side 20 of the body portion 18 between the first and second lateral ends 24, 26, as shown in FIG. 2. The inner strap 54 may include a pocket 58 configured to removably receive an insert 62. The insert 62 may contain a gel or other material and may be heated or cooled for providing heating or cooling therapy for the user's wrist 11 and/or hand 12.

The finger portion 22 may be attached to and extend from the first edge 25 of the body portion 18. The finger portion 22 may include a first side 29 (shown in FIG. 1) and a second side 31 (shown in FIG. 2). The first and second sides 29, 31 may cooperate to form first and second lateral ends 30, 34 and first and second edges 35, 36. A portion of the first edge 35 may be attached to the first edge 25 of the body portion 18 such that the first and second lateral ends 30, 34 are unattached to and movable relative to the body portion 18. As will be subsequently described, the first and second lateral ends 30, 34 can be wrapped around one or more of a user's fingers 37, 39 and may be releasably secured to each other via a buckle (not shown) or hook-and-loop retaining means (e.g., VELCRO®), for example, or any other suitable retaining means.

The spar 46 may be an elongated rigid member formed from a metallic or polymeric material, for example. The spar 46 may extend at least partially between the second edge 27 of the body portion 18 and the second edge 36 of the finger portion 22. In some embodiments, the spar 46 may be attached to the first sides 19, 29 or second sides 20, 31 of the body portion 18 and finger portion 22. In other embodiments, the spar 46 can be received in a pocket between the first sides 19, 29 and the second sides 20, 31.

With continued reference to FIGS. 1-5, operation of the brace 10 will be described in detail. The brace 10 may be worn by a user to treat injuries, degenerative conditions and/or other conditions such as carpal tunnel syndrome, for example. The brace 10 may be secured to the user's wrist 11, hand 12, and one or more fingers 37, 39 to support the wrist 11 and fingers 37, 39 and restrict movement of the wrist 11 and restrict movement of the fingers 37, 39 relative to a palm of the hand 12. Such support and restriction of motion may facilitate healing in the nerves, muscles, and/or other tissues in the wrist 11 and hand 12.

As shown in FIG. 3, the user may place his or her wrist 11 and hand 12 on the second side 20 of the body portion 18 and the user may place his or her middle and ring fingers 37, 39, for example, on the second side 31 of the finger portion 22 such that dorsal sides of the wrist 11, hand 12 and the middle and ring fingers 37, 39 are in contact with the second sides 20, 31 and are generally aligned with the spar 46. The user may insert his or her thumb 13 through the aperture 66, as shown in FIG. 3.

With the user's wrist 11, hand 12 and fingers 37, 39 in the position described above, the inner strap 54 may be wrapped around the wrist 11 and secured to the first side 19 of the first lateral end 24. In this manner, the insert 62 may be in heat transfer relation (for example, where the insert 62 provides either hot or cold therapy) with a palmar side of the wrist 11. As described above, the insert 62 may be heated or cooled prior to securing the brace 10 to the user's wrist 11.

Next, the brace 10 may be more firmly secured onto the wrist 11 and hand 12 by wrapping the first lateral end 24 around a circumference of the wrist 11 and at least a portion of the hand 12, as shown in FIGS. 4 and 5. The second lateral end 26 may or may not include a hook-and-loop retaining means (e.g., VELCRO®) for attachment to the first lateral end 24. The first and second outer straps 38, 42 may be wrapped around the body portion 18 and the user's wrist 11 and/or hand 12 and may be removably attached to the first side 19 of the body portion 18. The first lateral end 30 and second lateral end 34 of the finger portion 22 may envelope the middle and ring fingers 37, 39 by wrapping the first and second lateral ends 30, 34 around the circumference of the fingers 37, 39. The first lateral end 30 may be removably attached to the second lateral end 34 on the palmar side of the fingers 37, 39 to secure the finger portion 22 to the middle and ring fingers 37,39.

When the brace 10 is secured on the wrist 11, hand 12, and fingers 37, 39, the spar 46 may be aligned with a posterior aspect of a radiocarpal joint overlying a dorsum of a carpus. The spar 46 may restrict movement of the wrist 11 and fingers 37, 39 and may align the wrist 11 and fingers 37, 39 in a neutral position, plus or minus two degrees. A neutral position may be defined as a position in which the wrist 11 and/or fingers 37, 39 are in approximately flat or planar positions (e.g., the wrist 11, the dorsal side of the hand 12, and/or the fingers 37, 39 are generally coplanar with or straight relative to the user's forearm). For example, the spar 46 may be approximately flat or planar, or the spar 46 may form an angle of approximately two degrees or less at the wrist 11. By supporting the middle and ring fingers 37, 39 in a straight, neutral position, metacarpophalangeal joints (knuckles) on the index and pinky fingers 40, 41 will also be aligned in a straightened position due to anatomical factors. If the middle and ring fingers 37, 39 are supported by the finger portion 22 in the neutral position, the index and pinky fingers 40, 41 will naturally rest in the neutral position also. Further, the brace 10 may cover knuckles on the hand 12 where the fingers 37, 39, 40, 41 meet the hand 12 (i.e., the base knuckles or first joints) and help to support the pinky and ring fingers 40, 41 in the neutral position. Therefore, the same result can be achieved by only restricting two fingers 37, 39 instead of four which may be more comfortable for the user.

Figure 8:
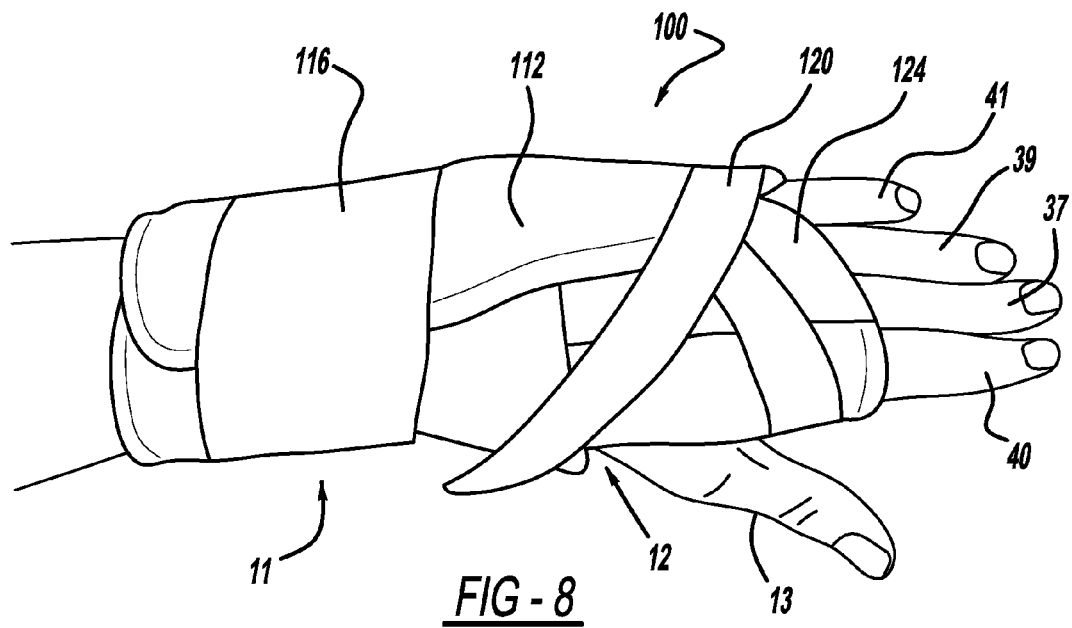
FIG. 8 is a perspective view of the brace secured to a user's limb according to the principles of the present disclosure.

With reference to FIGS. 6-8, another brace 100 is provided and may include a body portion 102 and a spar 124. The body portion 102 may include a flexible sheet 104 formed from a fabric such as the foam material, for example, and may be capable of bi-directional elastic deformation.

The body portion 102 may include a first side 105 (shown in FIG. 6) and a second side 106 (shown in FIG. 7). The first and second sides 105, 106 may cooperate to form a first lateral end 108, a second lateral end 112, a first edge 110, and a second edge 114. An aperture 128 may be formed in the body portion 102 between the first and second lateral ends 108, 112 and may extend through the first and second sides 105, 106. In some embodiments, the aperture 128 may be disposed closer to the first edge 110 than the second edge 114.

The body portion 102 may also include first outer strap 116, a second outer strap 120, and an inner strap 182. The first and second outer straps 116, 120 may be attached to the body portion 102 at or near the second lateral end 112. The first and second outer straps 116, 120 may be releasably secured to the first side 105 of the body portion via a buckle (not shown) or via hook-and-loop retaining means (e.g., VELCRO®) or any other suitable retaining means to secure the body portion to the user's wrist 11 and hand 12, as shown in FIG. 8.

The inner strap 182 may extend from the second side 106 of the body portion 102 between the first and second lateral ends 108, 112 as shown in FIG. 7. The inner strap 182 may or may not be angled in order to maximally cover the palmar surface of the hand and forearm. The inner strap may include a pocket 136 configured to removably receive the insert 62 (shown in FIG. 2). The insert may contain a gel or other material and may be heated or cooled for providing heating or cooling therapy for the user's wrist 11 and/or hand 12.

The spar 124 may be an elongated rigid member formed from a metallic or polymeric material, for example. The spar 124 may extend at least partially between the first and second edge 110, 114. In some embodiments, the spar 124 may be attached to the first side 105 or second side 106 of the body portion 102. In other embodiments, the spar 124 may be received in a pocket between the first side 105 and second side 106.

With continued reference to FIGS. 6-8, operation of the brace 100 will be described in detail. The brace 100 may be worn by a user to treat injuries, degenerative conditions and/or other conditions such as carpal tunnel syndrome, for example, when more mobility in the fingers is desired. The brace 100 may be secured to the user's wrist 11 and hand 12 to support the wrist 11 and restrict movement of the wrist 11 relative to the palm of the hand 12. Such support and restriction of motion may facilitate healing the nerves, muscles, and/or other tissues in the wrist 11 and hand 12.

The user may place his or her wrist 11 and hand 12 on the second side 106 of the body portion 102 such that dorsal sides of the wrist 11 and hand 12 are in contact with the second side 106 and are generally aligned with the spar 124. The user may insert his or her thumb 13 through the aperture 128.

With the user's wrist 11 and hand 12 in the position described above, the inner strap 182 may be wrapped around the wrist 11 and secured to the first side 105 of the first lateral end 108. In this manner, the insert 62 may be in heat transfer relation (for example, where the insert 62 provides either hot or cold therapy) with a palmar side of the wrist 11. As described above, the insert 62 may be heated or cooled prior to securing the brace 100 to the user's wrist 11.

Next, the brace may be more firmly secured onto the wrist 11 and hand 12, as shown in FIG. 8, by wrapping the second lateral end 112 around a circumference of the wrist 11 and at least a portion of the hand 12. The second lateral end 112 may or may not include a hook-and-loop retaining means (e.g., VELCRO®) for attachment to the first lateral end 108. The first and second outer straps 116, 120 may be wrapped around the body portion 102 and the user's wrist 11 and/or hand 12 and may be removably attached to the first side 105 of the body portion 102.

In some embodiments, the second outer strap 120 may be long enough to secure a bag of ice or any other cold or hot object to the first side 105 of the body portion 102. The second outer strap 120 may be angled (for example, at 45 degrees) across the wrist to apply heat or cold therapy to a distal side of the wrist.

When the brace 100 is secured on the wrist 11 and hand 12, the spar 124, may be aligned with the posterior of the radiocarpal joint and the dorsal of the carpus. The spar 124 may restrict the movement of the wrist 11 and may align the wrist 11 in a neutral position. For example only, the spar 46 may be approximately flat or planar, or may form a an angle of approximately two degrees or less at the wrist 11.

When secured on the wrist 11 and hand 12, the brace 100 may allow unrestricted movement of the fingers 37, 39, 40, 41. The brace 100 may cover a portion of the hand 12 between the wrist 11 and a proximal palmar crease 16 (reference FIG. 3) on the palmar side of the user's hand to allow unrestricted movement of the fingers 37, 39, 40, 41. The knuckles on the user's hand 12 where the fingers 37, 39, 40, 41 meet the hand 12 (i.e., the base knuckles or first joints) may be exposed to allow unrestricted movement of the fingers 37, 39, 40, 41. The proximal palmar crease 16 may also be exposed to allow unrestricted movement of the fingers 37, 39, 40, 41.

Figure 9:
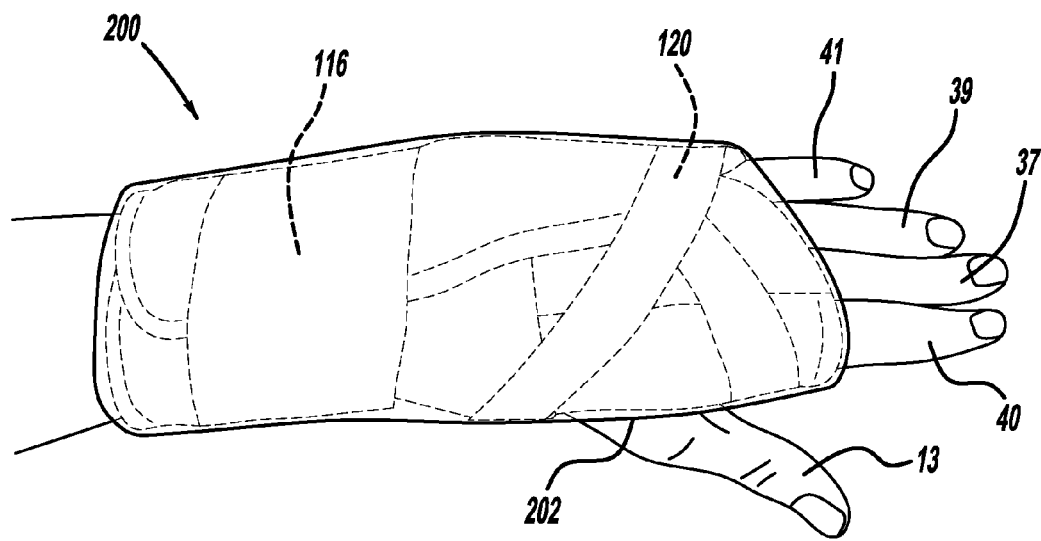
FIG. 9 is a perspective view of a sleeve covering the brace of FIG. 8.

With reference to FIG. 9, a sleeve 200 is provided that may be adapted to receive the hand 12 and wrist 11 and cover the brace 100 or the brace 10. The sleeve 200 may include an aperture to receive the user's thumb 13 and may be formed from a fabric such as a bi-directionally stretchable elastomer, for example. The sleeve 200 may be designed in various patterns or colors that the user may select from. The sleeve 200 may protect the first and second outer straps 116, 120 from being snagged on foreign objects. The sleeve 200 may also protect the user from being scratched by the brace 100. Further, the variety of colors and patterns of sleeves provides cosmetic advantages.

Referring now to FIGS. 1-9, the braces 10, 100 can be packaged as a set or kit to treat injuries, degenerative conditions and/or other conditions such as carpal tunnel syndrome, for example. The sleeve 200 may also be included in the packaged set.

The brace 100 can be worn during times when the user may be relatively active, such as when restricting movement of the middle and ring fingers 37, 39 is not practical. For example, the user may wear the brace 100 during the daytime or while the user is at work. The brace 100 allows relatively unobstructed movement of all of the fingers 37, 39, 40, 41, which may allow the user to perform tasks such as driving or typing at a computer, for example. The location of the spar 124 on the dorsum (top) of the hand 12 will improve functionality of the hand during daytime activities such as typing on a computer or driving.

The brace 10 can be worn during times of relative inactivity when restriction of movement of the middle and ring fingers 37, 39 can be tolerated by the user. For example, the user may wear the brace 10 at nighttime and/or while the user is sleeping or relaxing at home, for example.

While the braces 10, 100 are described above as including one or more generally flat sheets 14, 15, 104 having first and second ends that can be wrapped around the user's wrist, and/or fingers (in some embodiments) and secured to each other, in other embodiments, the braces 10, 100 may be formed as continuous, elastic sleeves that can be slid onto the user's wrist, hand, and/or fingers. In such embodiments, the braces 10, 100 may be sized to accommodate specific users.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A brace comprising:
   a body portion including a first flexible sheet configured to receive at least portions of a user's wrist and hand and restricting movement of the wrist;
   a finger portion including a second flexible sheet attached to said first flexible sheet, said finger portion being configured to be wrapped around only a user's digitus tertius and digitus annularis and restrict movement of the digitus tertius and digitus annularis and maintain the digitus tertius and digitus annularis at a predetermined position relative to the wrist and hand;
   a rigid panel attached to the first flexible sheet at a location that corresponds to a dorsal side of a user's wrist and hand;
   an outer strap having a first end and a second end, the first end attached to a lateral end of the body portion; and
   an inner strap having a first end and a second end, the first end of the inner strap attached to the first flexible sheet between the rigid panel and the first end of the outer strap.

2. The brace of claim 1, wherein the rigid panel is attached to the finger portion and restricts movement of the digitus tertius and digitus annularis.

3. The brace of claim 2, wherein the inner strap is configured to be wrapped at least partially around the user's wrist to secure the flexible sheet thereon.

4. The brace of claim 1, wherein the predetermined position is a neutral position.

5. The brace of claim 4, wherein the body portion restricts movement of the wrist and maintains the wrist in a neutral position.

6. A therapy kit comprising:
   a first brace including a first body portion configured to be wrapped around a user's wrist and restrict movement of the wrist and maintain the wrist at a neutral position, said first brace allowing relative movement of all of the user's knuckles on all of the user's fingers relative to the wrist; and
   a second brace including a second body portion and a finger portion, said second body portion being configured to be wrapped around the user's wrist and restrict movement of the wrist and maintain the wrist at the neutral position, said second body portion including a first side extending between first and second lateral edges, and an inner strap, the inner strap attached to said first side between said first and second lateral edges, said finger portion being attached to said second body portion and being configured to be wrapped around only the user's digitus tertius and digitus annularis and restrict movement of the user's digitus tertius and digitus annularis relative to the wrist and maintain the digitus tertius and digitus annularis in an extended position,
   wherein the first and second braces are detached from each other and configured to be worn by the user independently of each other.

7. The therapy kit of claim 6, further comprising a cylindrical sleeve adapted to cover at least one of the first and second braces.

8. The brace of claim 6, wherein the inner strap is positioned during use to be in-line with one or more nerves associated with carpal tunnel syndrome to maximize thermal transfer.

* * * * *